United States Patent
Maldonado et al.

(10) Patent No.: US 8,450,286 B2
(45) Date of Patent: May 28, 2013

(54) METHOD FOR TREATING CANCERS HAVING HIGH GLUCOSE REQUIREMENTS EMPLOYING AN SGLT2 INHIBITOR AND COMPOSITIONS THEREOF

(75) Inventors: Mario Maldonado, Basel (CH); Paul Strumph, Moneta, VA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 308 days.

(21) Appl. No.: 12/933,013

(22) PCT Filed: Mar. 16, 2009

(86) PCT No.: PCT/US2009/037301
§ 371 (c)(1), (2), (4) Date: Sep. 16, 2010

(87) PCT Pub. No.: WO2009/117367
PCT Pub. Date: Sep. 24, 2009

(65) Prior Publication Data
US 2011/0015141 A1    Jan. 20, 2011

Related U.S. Application Data

(60) Provisional application No. 61/037,509, filed on Mar. 18, 2008.

(51) Int. Cl.
*A61K 31/7034* (2006.01)
*C07H 7/04* (2006.01)

(52) U.S. Cl.
USPC .......................................... 514/23; 536/1.11

(58) Field of Classification Search
None
See application file for complete search history.

(56) References Cited

U.S. PATENT DOCUMENTS

| | | | |
|---|---|---|---|
| 4,840,939 A * | 6/1989 | Leveen et al. | 514/25 |
| 6,414,126 B1 | 7/2002 | Ellsworth et al. | |
| 7,375,213 B2 * | 5/2008 | Deshpande et al. | 536/124 |
| 7,919,598 B2 * | 4/2011 | Gougoutas et al. | 536/1.11 |

OTHER PUBLICATIONS

Ehrenkranz et al. "Phlorizin: a review" Diabetes/Metabolism Research and Reviews (2005) vol. 21 pp. 31-38.*
Cao et al., "Glucose uptake inhibitor sensitizes cancer cells to daunorubicin and overcomes drug resistance in hypoxia" Cancer Chemotherapy and Pharmacology (2007) vol. 59 pp. 495-505.*
The Merck Manual of Diagnosis and Therapy, published 1999 by Merck Research Laboratories, pp. 973-977 and 989-995.*
Ishikawa, N. et al.: "SGLT Gene Expression in Primary Lung Cancers and Their Matastatic Lesions," Japanese Journal of Cancer Research, Japanese Cancer Association, Tokyo, JP, vol. 92, No. 8, Aug. 1, 2001, pp. 874-879.
Komoroski, B. et al.: "Dapagliflozin (BMS-512148), a selective SGLT2 Inhibitor, Inhibits glucose resorption and reduces fasting glucose in patients with type 2 diabetes mellitus," Diabetologia, vol. 50, No. Suppl. 1, Sep. 2007, p. S315.
Kler, L. et al.: "Clinical studies to assess safety, pharmacokinetics and pharmacodynamics of sergliflozin, a noel inhibitor of glucose reabsorption," Diabetologia, vol. 50, No. Suppl. 1, Sep. 2007, pp. S376-377.
Songping Han et al., "Dapagliflozin, a Selective SGLT2 Inhibitor, Improves Glucose Homeostasis in Normal and Diabetic Rats," Diabetes, 57, 1723-29 (2008).
Wei Meng et al., "Discovery of Dapagliflozin: A Potent Selective Renal Sodium-Dependent Glucose Cotransporter 2 (SGLT2) Inhibitor for the Treatment of Type 2 Diabetes," J. Med. Chem., 51, 1145-49 (2008).

* cited by examiner

*Primary Examiner* — Eric S Olson
(74) *Attorney, Agent, or Firm* — McDonnell Boehnen Hulbert & Berghoff LLP

(57) ABSTRACT

Methods are provided for treating cancers that have high glucose requirements and that express SGLT2 at levels higher than normal cells, such as metastatic cancers, for example, metastatic lung cancers, employing an SGLT2 inhibitor alone or in combination with a cytotoxic agent and to a composition containing a combination of an SGLT2 inhibitor and a cytotoxic agent.

24 Claims, 2 Drawing Sheets

Indirect comparison of GSK 869,682 and Dapagliflozin PGS

Urine glucose excretion in diabetic subjects treated with Dapagliflozin PGS

US 8,450,286 B2

METHOD FOR TREATING CANCERS HAVING HIGH GLUCOSE REQUIREMENTS EMPLOYING AN SGLT2 INHIBITOR AND COMPOSITIONS THEREOF

This application is a national phase application under 35 U.S.C. 371 of International Application No. PCT/US2009/037301, filed Mar. 16, 2009 which claims priority to U.S. provisional application 61/037,509, filed Mar. 18, 2008, the contents of which are hereby incorporated by reference.

FIELD OF THE INVENTION

The invention relates to a method for treating cancers that have high glucose requirements and that express SGLT2 at levels higher than normal cells, comprising administering an SGLT2 inhibitor alone or in combination with a cytotoxic agent, and to compositions thereof.

BACKGROUND OF THE INVENTION

It is known that cancer cells need increased glucose uptake and utilization as compared to normal cells. Uptake of glucose in cells, including cancer cells, is facilitated by glucose transporters including $Na^+$/glucose cotransporter-2 (SGLT2), that utilize the electrochemical sodium gradient to transport glucose against the cells internal concentration gradient.

Researchers have reported that SGLT2 expression was significantly higher in the metastatic lesions in the liver and lymph node than in the primary lung cancers. SGLT1 expression in the primary lung cancers and their metastatic lesions did not significantly differ. These results indicate that SGLT2 plays a role in glucose uptake in the metastatic lesions of lung cancer.

The inhibition of SGLT2 as a means to reduce glucose uptake in cancer cells represents a viable therapeutic method for treating cancers. Therefore, compounds or agents that inhibit SGLT2 are attractive targets for treating cancers that have increased expression of SGLT2, such as metastatic lesions associated with lung cancer.

SUMMARY OF THE INVENTION

In one aspect, the invention provides a method for treating cancers that express SGLT2 at a level higher than normal cells in a mammal comprising administering to the mammal in need of such treatment a therapeutically effective amount of an SGLT2 inhibitor.

In another aspect, the invention provides a method for treating cancers that express SGLT2 at higher levels than normal cells in a mammal comprising administering to the mammal in need of such treatment a therapeutically effective amount of a pharmaceutical composition comprising an SGLT2 inhibitor and at least one pharmaceutically acceptable carrier, excipient, or diluent.

In another aspect, the invention provides a method for treating cancers that express SGLT2 at higher levels than normal cells in a mammal comprising administering to the mammal in need of such treatment a therapeutically effective amount of an SGLT2 inhibitor and a cytotoxic agent where the cytotoxic agent is administered prior to, after, or concurrently with the SGLT2 inhibitor.

In another aspect, the invention provides a method for treating cancers that express SGLT2 at higher levels than normal cells in a mammal comprising administering to the mammal in need of such treatment a therapeutically effective amount of a pharmaceutical composition comprising an SGLT2 inhibitor, a cytotoxic agent and at least one pharmaceutically acceptable carrier, excipient, or diluent.

DETAILED DESCRIPTION OF THE INVENTION

Figure 1:
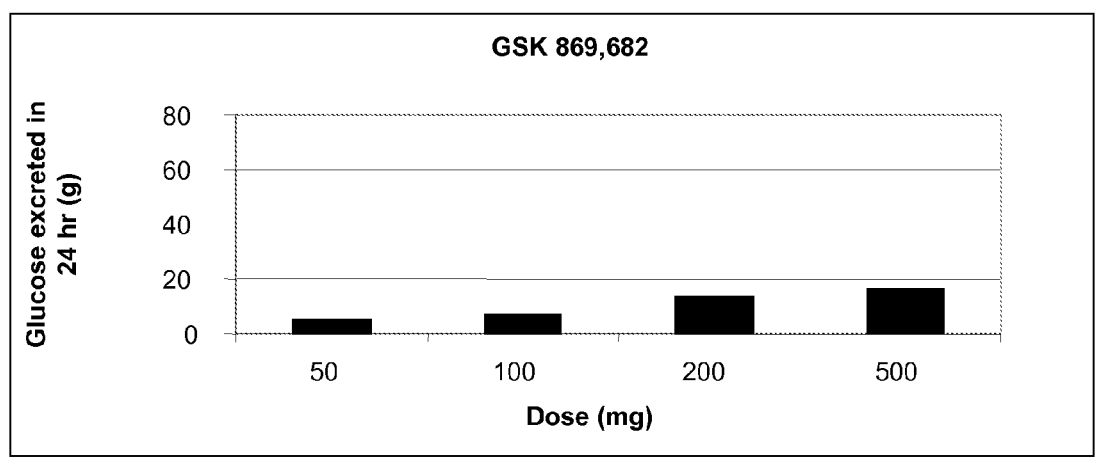
FIG. 1 depicts bar graphs showing an indirect comparison of the amount of glucose excretion in urine/day caused by each of the SGLT2 inhibitors GSK 869,682 and Compound Ia.
Figure 1:
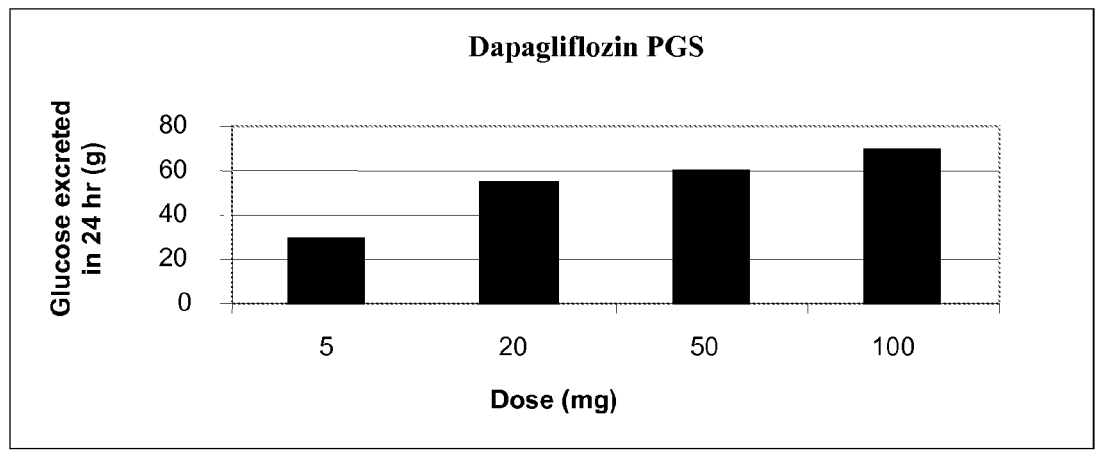

In one aspect, the invention provides a method for treating lung cancer metastatic lesions in a mammal comprising administering to the mammal in need of such treatment a therapeutically effective amount of an SGLT2 inhibitor.

In another aspect, the invention provides a method for treating lung cancer metastatic lesions in a mammal comprising administering to the mammal in need of such treatment a therapeutically effective amount of a pharmaceutical composition comprising an SGLT2 inhibitor and at least one pharmaceutically acceptable carrier, excipient, or diluent.

In another aspect, the invention provides a method for treating lung cancer metastatic lesions in a mammal comprising administering to the mammal in need of such treatment a therapeutically effective amount of an SGLT2 inhibitor and a cytotoxic agent where the cytotoxic agent is administered prior to, after, or concurrently with the SGLT2 inhibitor.

In another aspect, the invention provides a method for treating lung cancer metastatic lesions in a mammal comprising administering to the mammal in need of such treatment a therapeutically effective amount of a pharmaceutical composition comprising an SGLT2 inhibitor, a cytotoxic agent and at least one pharmaceutically acceptable carrier, excipient, or diluent.

In one aspect, the invention provides a method for treating lung cancer metastatic lesions in a human comprising administering to the human in need of such treatment a therapeutically effective amount of an SGLT2 inhibitor.

In another aspect, the invention provides a method for treating lung cancer metastatic lesions in a human comprising administering to the human in need of such treatment a therapeutically effective amount of a pharmaceutical composition comprising an SGLT2 inhibitor and at least one pharmaceutically acceptable carrier, excipient, or diluent.

In another aspect, the invention provides a method for treating lung cancer metastatic lesions in a human comprising administering to the human in need of such treatment a therapeutically effective amount of an SGLT2 inhibitor and a cytotoxic agent where the cytotoxic agent is administered prior to, after, or concurrently with the SGLT2 inhibitor.

In another aspect, the invention provides a method for treating lung cancer metastatic lesions in a human comprising administering to the human in need of such treatment a therapeutically effective amount of a pharmaceutical composition comprising an SGLT2 inhibitor, a cytotoxic agent and at least one pharmaceutically acceptable carrier, excipient, or diluent.

In one aspect, the invention provides a method for treating lung cancer metastatic lesions in the liver of a human comprising administering to the human in need of such treatment a therapeutically effective amount of an SGLT2 inhibitor.

In another aspect, the invention provides a method for treating lung cancer metastatic lesions in the liver of a human comprising administering to the human in need of such treatment a therapeutically effective amount of a pharmaceutical composition comprising an SGLT2 inhibitor and at least one pharmaceutically acceptable carrier, excipient, or diluent.

In another aspect, the invention provides a method for treating lung cancer metastatic lesions in the liver of a human comprising administering to the human in need of such treatment a therapeutically effective amount of an SGLT2 inhibitor and a cytotoxic agent where the cytotoxic agent is administered prior to, after, or concurrently with the SGLT2 inhibitor.

In another aspect, the invention provides a method for treating lung cancer metastatic lesions in the liver of a human comprising administering to the human in need of such treatment a therapeutically effective amount of a pharmaceutical composition comprising an SGLT2 inhibitor, a cytotoxic agent and at least one pharmaceutically acceptable carrier, excipient, or diluent.

In one aspect, the invention provides a method for treating lung cancer metastatic lesions in the lymph nodes of a human comprising administering to the human in need of such treatment a therapeutically effective amount of an SGLT2 inhibitor.

In another aspect, the invention provides a method for treating lung cancer metastatic lesions in the lymph nodes of a human comprising administering to the human in need of such treatment a therapeutically effective amount of a pharmaceutical composition comprising an SGLT2 inhibitor and at least one pharmaceutically acceptable carrier, excipient, or diluent.

In another aspect, the invention provides a method for treating lung cancer metastatic lesions in the lymph nodes of a human comprising administering to the human in need of such treatment a therapeutically effective amount of an SGLT2 inhibitor and a cytotoxic agent where the cytotoxic agent is administered prior to, after, or concurrently with the SGLT2 inhibitor.

In another aspect, the invention provides a method for treating lung cancer metastatic lesions in the lymph nodes of a human comprising administering to the human in need of such treatment a therapeutically effective amount of a pharmaceutical composition comprising an SGLT2 inhibitor, a cytotoxic agent and at least one pharmaceutically acceptable carrier, excipient, or diluent.

In another aspect, the invention provides a use of an SGLT2 inhibitor in the manufacture of a medicament for treating lung cancer metastatic lesions.

In another aspect, the invention provides a combination of a SGLT2 inhibitor and a cytotoxic agent as a medicament for treating lung cancer metastatic lesions, where the cytotoxic agent is administered prior to, after, or concurrently with the SGLT2 inhibitor.

In another aspect, the invention provides a use of an SGLT2 inhibitor in the manufacture of a medicament for treating lung cancer metastatic lesions in the liver.

In another aspect, the invention provides a combination of a SGLT2 inhibitor and a cytotoxic agent as a medicament for treating lung cancer metastatic lesions in the liver, where the cytotoxic agent is administered prior to, after, or concurrently with the SGLT2 inhibitor.

In another aspect, the invention provides a use of an SGLT2 inhibitor in the manufacture of a medicament for treating lung cancer metastatic lesions in the lymph nodes.

In another aspect, the invention provides a combination of a SGLT2 inhibitor and a cytotoxic agent as a medicament for treating lung cancer metastatic lesions in the lymph nodes, where the cytotoxic agent is administered prior to, after, or concurrently with the SGLT2 inhibitor.

The SGLT2 inhibitor is employed in a weight ratio to the optional cytotoxic agent in an amount within the range from about 200:1 to about 0.1:1, preferably from about 100:1 to about 0.2:1.

The dosage for the cytotoxic agent (used in combination with the SGLT2 inhibitor) will be the recommended doses for such cytotoxic agents as disclosed in the latest PHYSICIANS' DESK REFERENCE (PDR) or REMINGTON'S PHARMACEUTICAL SCIENCES (Mack Publishing Co., Easton, Pa.).

The SGLT2 inhibitor employed in the above-defined methods of the invention will not cause hypoglycemia in non-diabetic humans that is a human who does not suffer from hyperglycemia, and will not cause hypoglycemia in diabetic humans as well.

In preferred embodiments of all aspects of the invention, the SGLT2 inhibitor will be administered in amounts below the therapeutic amount (sub-therapeutic amount) as prescribed in generally accepted medical practice for treating diabetes.

The SGLT2 inhibitor employed in the invention is selective for SGLT2 relative to SGLT-1. Higher SGLT2: SGLT-1 selectivity ratios result in greater effectiveness at eradicating cancer cells.

In carrying out the methods of the invention for treating cancers which express SGLT2 at levels higher than normal cells, the SGLT2 inhibitor may be administered to a patient in need of treatment in a cancer treating amount which can be as high as that which may be used to treat cancers but less than an amount which could cause hypoglycemia. The daily dose may be lowered as successful treatment of cancer cells is achieved. For example, depending upon the patient, and the specific SGLT2 inhibitor employed, the SGLT2 inhibitor may be orally administered in a cancer treating amount from about 1 to about 1000 mg per day, preferably from about 2 to about 400 mg/day, preferably 2.5 to about 75 mg/day, and more preferably 20 to about 50 mg/day, which can be administered in a single dose or in the form of individual doses from 1 to 4 times per day.

The SGLT2 inhibitor may be administered by injection to a patient in a cancer treating amount from about 1 to about 100 mg/day, preferably from about 1 to about 30 mg/day.

The SGLT2 inhibitor suitable for use in accordance with the invention will be a C-arylglucoside or an O-arylglucoside.

Examples of C-arylglucoside (also referred to as C-glucosides) SGLT2 inhibitors which may be employed in the method of the invention, include, but are not limited to the following:

1) Compound I or dapagliflozin

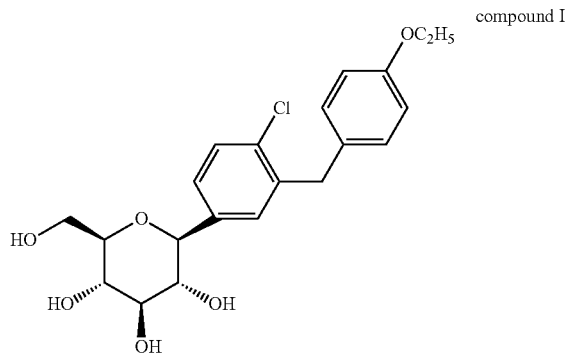 [SMILES: CCOc1ccc(Cc2cc([C@@H]3O[C@H](CO)[C@@H](O)[C@H](O)[C@H]3O)ccc2Cl)cc1]

compound I preferred for use in the invention and its corresponding tetraacetate shown below as compound II

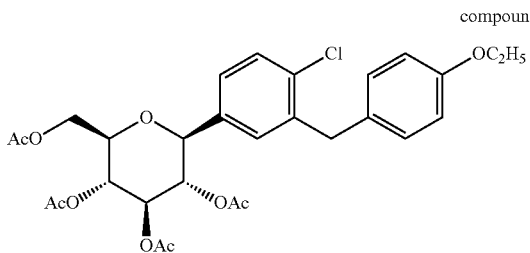

compound II as disclosed in U.S. Pat. No. 6,515,117, (PCT/US03/15591) the disclosure of which is incorporated herein by reference in its entirety for any purpose.

2) Compounds of formula III:

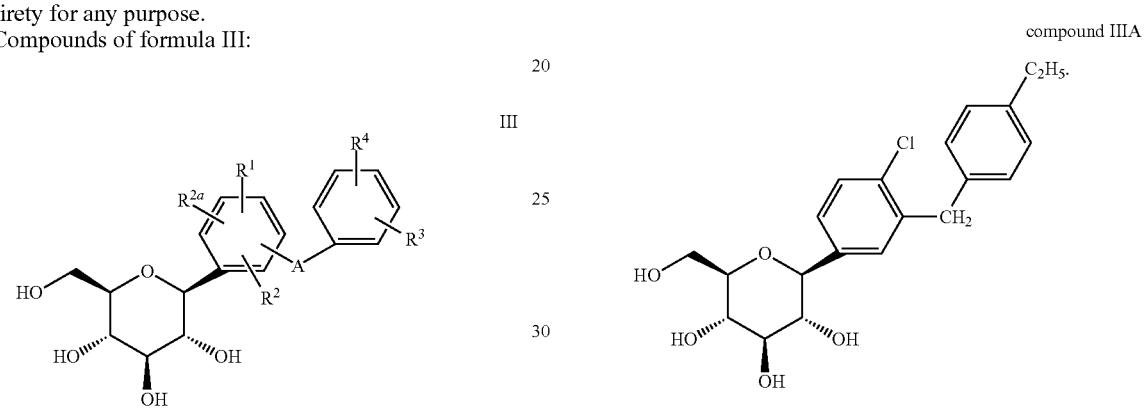

III wherein $R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five-, six- or seven-membered carbocycle or heterocycle which may contain 1 to 4 heteroatoms in the ring which are N, O, S, SO, and/or $SO_2$;

$R^3$ and $R^4$ are independently hydrogen, OH, $OR^{5a}$, OAryl, $OCH_2$Aryl, alkyl, cycloalkyl, $CF_3$, —$OCHF_2$, —$OCF_3$, halogen, —CN, —$CO_2R^{5b}$, —$CO_2H$, —$COR^{6b}$, —CH(OH)$R^{6c}$, —CH($OR^{5h}$)$R^{6d}$, —$CONR^6R^{6a}$, —$NHCOR^{5c}$, —$NHSO_2R^{5d}$, —$NHSO_2$Aryl, aryl, —$SR^{5e}$, —$SOR^{5f}$, —$SO_2R^{5g}$, —$SO_2$Aryl, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$;

A is O, S, NH, or $(CH_2)_n$ where n is 0-3, and pharmaceutically-acceptable salts thereof, all stereoisomers thereof, and all prodrug esters thereof.

The compounds of formula III as defined above also include compounds wherein where A is $(CH_2)_n$ where n is 0, 1, 2, or 3 or A is 0, and at least one of $R^1$, $R^2$, and $R^{2a}$ is OH or $OR^5$, then at least one of $R^1$, $R^2$, and $R^{2a}$ is $CF_3$, $OCF_3$, or $OCHF_2$ and/or at least one of $R^3$ and $R^4$ is $CF_3$, —$OCHF_2$, $CH(OR^{5h})R^{6d}$, CH(OH)$R^{6c}$, $COR^{6b}$, —CN, —$CO_2R^{5b}$, —$NHCOR^{5c}$, —$NHSO_2R^{5d}$, —$NHSO_2$Aryl, aryl, —$SR^{5e}$, —$SOR^{5f}$, —$SO_2R^{5g}$ or —$SO_2$Aryl.

Preferred compounds of formula III as defined above compounds wherein where A is $(CH_2)_n$ where n is 0, 1, 2, or 3 or A is O, and at least one of $R^1$, $R^2$, $R^{2a}$, $R^3$ and $R^4$ is OH or $OR^5$, then at least one of R', $R^2$, and $R^{2a}$ is $CF_3$, $OCF_3$, or $OCHF_2$ and/or at least one of $R^3$ and $R^4$ is $CF_3$, —$OCHF_2$, —CN, —$CO_2R^{5b}$, $CH(OR^{5h})R^{6d}$, —$NHCOR^{5c}$, —$NHSO_2R^{5d}$, —$NHSO_2$Aryl, aryl, —$SR^{5e}$, —$SOR^{5f}$, —$SO_2R^{5g}$, —$SO_2$Aryl or halogen.

Preferred for use herein is compound IIIA, shown below, disclosed in U.S. Pat. No. 6,414,126 (PCT/US00/27187).

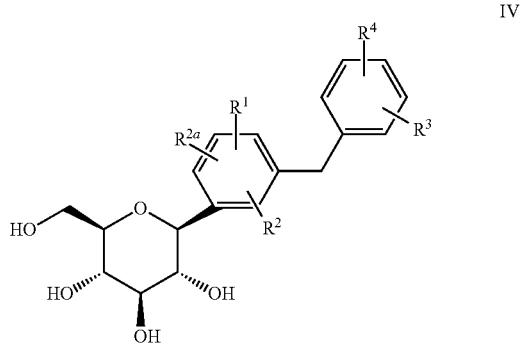

compound IIIA

3) C-aryl glucosides that are crystalline complexes of amino acids, such as L-proline and D-phenylalanine complexes, as disclosed in U.S. Pat. No. 6,774,112 (PCT/US02/11066) (the disclosure of which is incorporated herein by reference in its entirety) as follows:

IV wherein $R^1$, $R^2$ and $R^{2a}$ are independently hydrogen, OH, $OR^5$, alkyl, —$OCHF_2$, —$OCF_3$, —$SR^{5a}$ or halogen;

$R^3$ and $R^4$ are independently hydrogen, OH, $OR^{5b}$, alkyl, cycloalkyl, $CF_3$, —$OCHF_2$, —$OCF_3$, halogen, —$CONR^6R^{6a}$, —$CO_2R^{5c}$, —$CO_2H$, —$COR^{6b}$, —CH(OH)$R^{6c}$, —CH($OR^{5d}$)$R^{6d}$, —CN, —$NHCOR^{5e}$, —$NHSO_2R^{5f}$, —$NHSO_2$Aryl, —$SR^{5g}$, —$SOR^{5h}$, —$SO_2R^{5f}$, or a five-, six- or seven-membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, SO$_2$;

$R^5$, $R^{5a}$, $R^{6b}$, $R^{6c}$, $R^{6d}$, $R^{6e}$, $R^{5f}$, $R^{5g}$, $R^{5h}$ and $R^{5i}$ are independently alkyl; and $R^6$, $R^{6a}$, $R^{6b}$, $R^{6a}$ and $R^{6d}$ are independently hydrogen, alkyl, aryl, alkylaryl or cycloalkyl, or $R^6$ and $R^{6a}$ together with the nitrogen to which they are attached form an annelated five-, six- or seven-membered heterocycle which may contain 1 to 4 heteroatoms in the ring which are N, O, S, SO, and/or SO$_2$.

Preferred compounds of formula IV include the L-proline and D-phenylalanine complexes wherein $R^1$ is p-Cl, and $R^3$ is p-C$_2$H$_5$ or p-OC$_2$H$_5$;

4) Glucopyranosyl-substituted benzene derivatives or salts thereof as disclosed in US 2005/0209166 (the disclosure of which is incorporated by reference in its entirety) as follows:

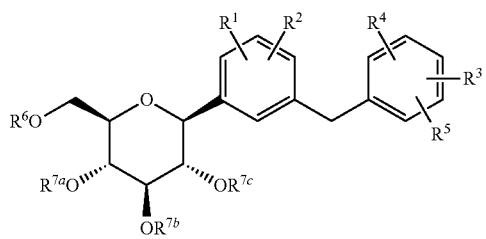

V wherein $R^1$, $R^2$, $R^3$, $R^4$, $R^5$, $R^6$, $R^{7a}$, $R^{7b}$ and $R^{7a}$ are as defined in US 2005/0209166.

5) D-pyranosyl-substituted phenyls as disclosed in US 2006/0074031 (the disclosure of which is incorporated herein by reference in its entirety) as follows:

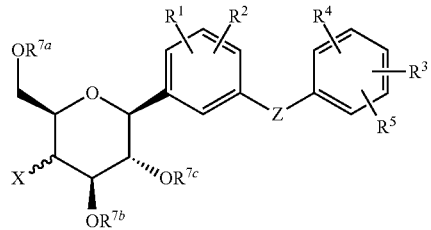

VI wherein $R^1$, $R^2$, $R^3$, $R^4$, $R^5$, $R^6$, $R^{7a}$, $R^{7b}$, $R^{7c}$, X and Z are as defined in US 2006/0074031.

6) D-xylopyranosyl-substituted cycles or salts thereof as disclosed in US 2006/0035841 (the disclosure of which is incorporated herein by reference in its entirety) as follows:

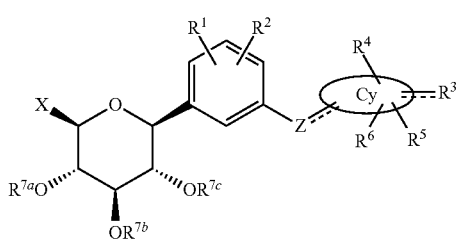

VII wherein

--- denotes a single or double bond, and

Cy, $R^1$, $R^2$, $R^3$, $R^4$, $R^5$, $R^6$, $R^{7a}$, $R^{7b}$, $R^{7a}$, X and Z are as defined in US 2006/0035841.

7) D-xylopyranosyl-substituted phenyls or salts thereof as disclosed in US 2006/0009400 (the disclosure of which is incorporated herein by reference in its entirety) as follows

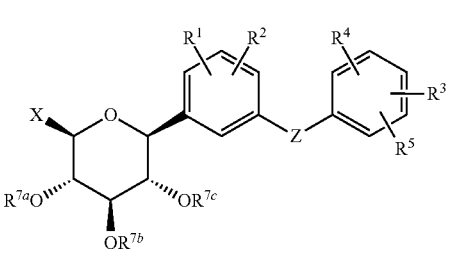

VIII wherein $R^1$, $R^2$, $R^3$, $R^4$, $R^5$, $R^{7a}$, $R^{7b}$, $R^{7c}$, X and Z are as disclosed in US 2006/0009400.

8) D-glucopyranosyl-phenyl-substituted cycles and salts thereof as disclosed in US 2006/0025349 (the disclosure of which is incorporated herein by reference in its entirety) as follows:

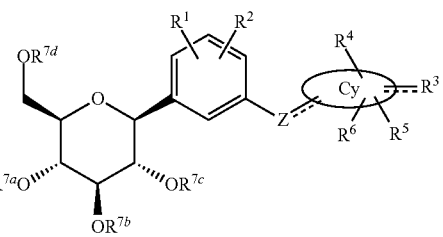

IX wherein

--- denotes a single or double bond, and

Cy, $R^1$, $R^2$, $R^3$, $R^4$, $R^5$, $R^6$, $R^{7a}$, $R^{7b}$, $R^{7c}$, $R^{7d}$ and Z are defined in US 2006/0025349.

9) C-glycoside derivatives and salts thereof as disclosed in US 2006/0122126 (the disclosure of which is incorporated herein by reference in its entirety) as follows:

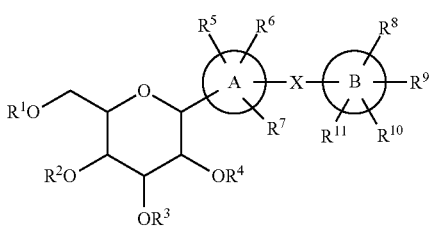

X wherein $R^1$, $R^2$, $R^3$, $R^4$, $R^5$, $R^6$, $R^7$, $R^8$, $R^9$, $R^{10}$, $R^{11}$, X, A and B are as defined in US 2006/0122126.

10) D-xylopyranosyl-substituted phenyls as disclosed in US 2006/0019948 (the disclosure of which is incorporated herein by reference in its entirety) as follows:

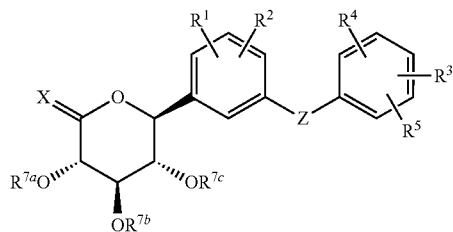

wherein $R^1$, $R^2$, $R^3$, $R^4$, $R^5$, $R^{7a}$, $R^{7b}$, $R^{7c}$, X and Z are as defined in US 2006/0019948.

Examples of O-glucoside SGLT2 inhibitors which may be employed in the method of the invention include, but are not limited to the following:

1) 5-Thio-β-D-glucopyranosides or salts or hydrates thereof as disclosed in US 2006/0194809 (the disclosure of which is incorporated by reference in its entirety) as follows:

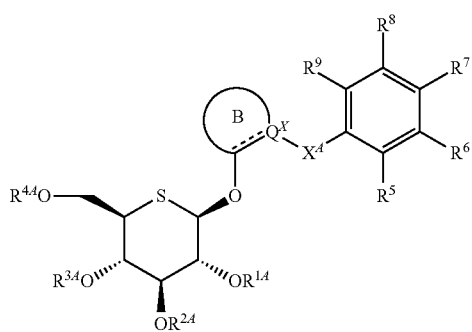

wherein $R^{1A}$, $R^{2A}$, $R^{3A}$, $R^{4A}$, $R^5$, $R^6$, $R^7$, $R^8$, $R^9$, $Q^x$, $X^A$ and B are as defined in US 2006/0194809.

2) Glucopyranyloxybenzene derivatives as disclosed in WO 03/01180 (the disclosure of which is incorporated by reference in its entirety) as follows:

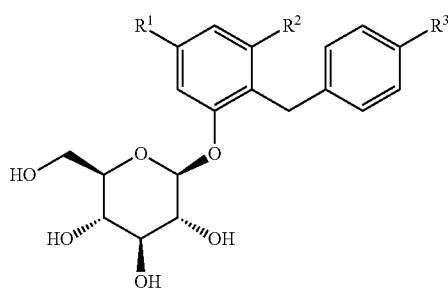

wherein $R^1$ represents hydrogen, hydroxyl, optionally substituted amino, cyano, carbamoyl, optionally substituted lower alkyl, optionally substituted lower alkoxy, or optionally substituted cyclic amino;

$R^2$ represents hydrogen or lower alkyl; and $R^3$ represents optionally substituted aryl, optionally substituted cycloalkyl, an optionally substituted aliphatic heterocyclic group, or an optionally substituted aromatic heterocyclic group, a pharmacologically acceptable salt of the derivative, or a prodrug of either.

3) Pyrazole derivatives or salts thereof as disclosed in U.S. Pat. No. 6,908,905 (the disclosure of which is incorporated herein by reference in its entirety) as follows:

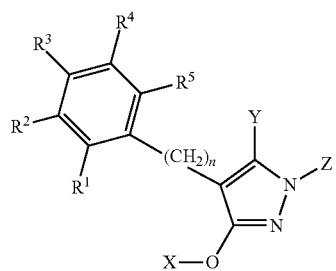

or

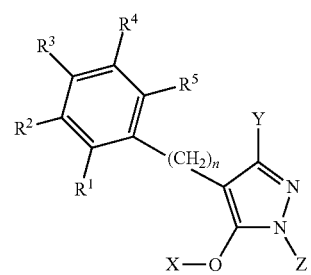

wherein X represents β-D-glucopyranosyl group, wherein one or more hydroxyl groups may be acylated; Y represents a lower alkyl group or a perfluoro lower alkyl group; Z represents a cyclic alkyl group which may have a substituent(s), a cyclic unsaturated alkyl group which may have a substituent(s), a lower alkyl group having a cyclic alkyl group which may have a substituent(s), or a lower alkyl group having a cyclic unsaturated alkyl group which may have a substituent(s); $R^1$ to $R^5$ may be the same or different and each represent a hydrogen atom, a lower alkyl group, a perfluoro lower alkyl group, a lower alkyloxy group, a perfluoro lower alkoxyl group, a lower alkylthio group, a perfluoro lower alkylthio group, a lower alkylamino group, a halogen group, a lower alkanoyl group, an alkenyl group, a cyclic alkenyl group, an alkynyl group, a phenyl group which may have a substituent(s), or a lower alkoxycarbonyl group; and n is an integer of 0 to 3 including:

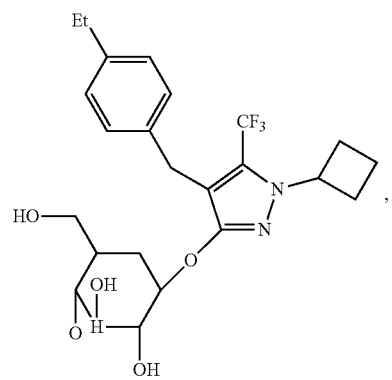

-continued

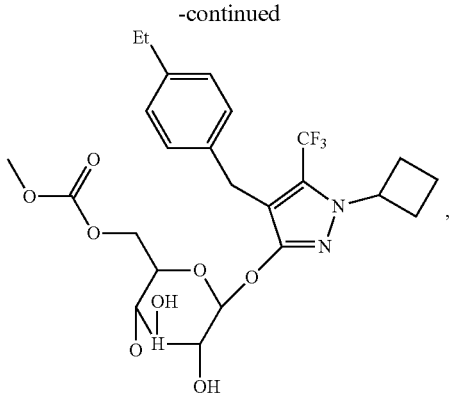

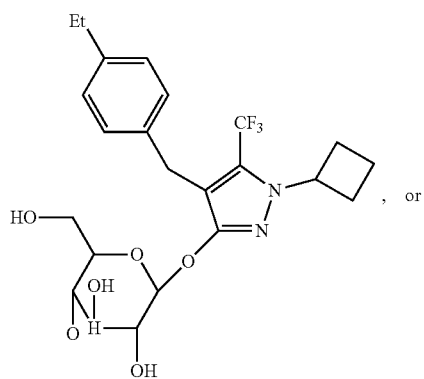, or

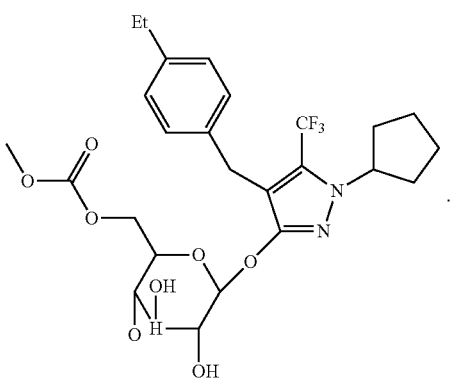

4) Pyrazole compounds or salts thereof as disclosed in U.S. Pat. No. 6,815,428 (the disclosure of which is incorporated herein by reference in its entirety) as follows:

XVI

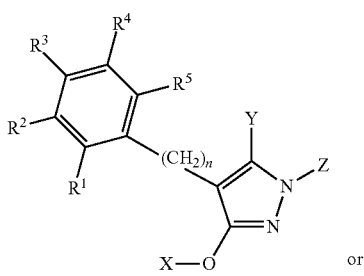 or

-continued

XVII

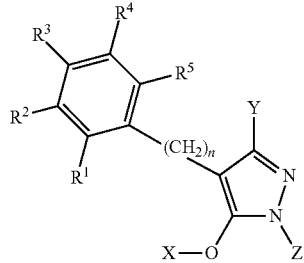

wherein X represents a β-D-glucopyranosyl group, of which one or more hydroxyl groups may be acylated or a β-D-glucuronyl group, of which one or more hydroxyl groups may be acylated and a carboxyl group may be esterified; Y represents a lower alkyl group or a perfluoro lower alkyl group; Z represents a hydrogen atom, a lower alkyl group, a perfluoro lower alkyl group, an aralkyl group or a phenyl group; $R^1$, $R^2$, $R^4$ and $R^5$ may be the same or different and each represents a hydrogen atom, a lower alkyl group, a perfluoro group, a lower alkoxy group, a fluoro lower alkoxy group, a lower alkylthio group, a perfluoro lower alkylthio group, a lower alkyl amino group, a halogen group, a lower alkanoyl group, a lower alkenyl group or a lower alkynyl group; and n represents an integer from 0 to 3, wherein at least one of $R^1$, $R^2$, $R^4$ and $R^5$ represents a lower alkyl group having 1 to 6 carbon atoms, lower alkylthio group having 1 to 6 carbon atoms, halogen atom, lower alkoxy group lower alkenyl group or lower alkynyl group; and $R^3$ represents a lower alkyl group having a 1 to 6 carbon atoms, a lower alkylthio group having 1 to 6 carbon atoms, a halogen atom, a lower alkoxy group, a lower alkenyl group, or a lower alkynyl group.

5) O-glucosylated benzamides or salts thereof as disclosed in U.S. Pat. No. 6,555,519 (the disclosure of which is incorporated herein by reference in its entirety) as follows:

XVIII

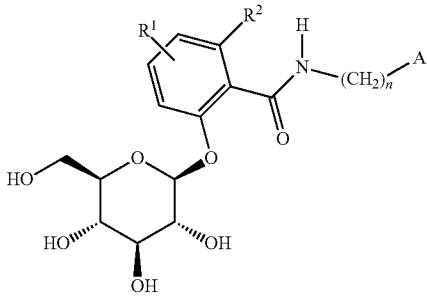

wherein
n is 0, 1 or 2;
A is

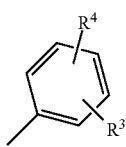

or heteroaryl which may contain 1 to 4 heteroatoms in the ring which may be selected from N, O, S, SO, and/or $SO_2$ bearing substituents $R^3$ and $R^4$;

$R^1$ is selected from hydrogen, $OR^S$, lower alkyl, aryl, arylalkyl, $NHCOR^5$, $NR^6R^{6a}$, or halogen;

$R^2$ is selected from hydrogen, OH, $OR^{5a}$, or lower alkyl;

$R^3$ an $R^4$ are the same or different and are independently selected from hydrogen, OH, $OR^{5b}$, OAryl, $OCH_2$Aryl, lower alkyl, cycloalkyl, aryl, arylalkyl, $CF_3$, $-SCF_3$, $-OCHF_2$, $-OCF_3$, halogen, $-CN$, $-CO_2R^{5c}$, $-CO_2H$, $-CONR^{6b}$, $R^{6c}$, $-NR^{6d}R^{6e}$, $-SO_2NH_2$, $-NHCOR^{5d}$, $-NHSO_2R^{5e}-$NHSO_2$Aryl, $-SR^{5f}$, $-SOR^{5g}$, $-SO_2R^{5h}$, $-SO_2$Aryl, $-OCH_2CO_2R^{5i}$, $-OCH_2CO_2H$, $-OCH_2CONR^{6f}R^{6g}$, $-OCH_2CH_2NR^{6h}R^{6i}$, or a five-, six- or seven-membered heterocycle which may contain 1 to 4 heteroatoms in the ring which are N, O, S, SO, and/or $SO_2$, or $R^3$ and $R^4$ together with the carbons to which they are attached form an annelated five-, six- or seven-membered carbocycle or heterocycle which may contain 1 to 4 heteroatom in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5i}$, and $R^{5i}$ are independently lower alkyl; and $R^6$, $R^{6a}$, $R^{6b}$, $R^{6c}$, $R^{6d}$, $R^{6e}$, $R^{6f}$, $R^{6g}$, $R^{6h}$, and $R^{6i}$ are the same or different and are independently selected from hydrogen, alkyl, aryl, arylalkyl or cycloalkyl.

6) O-aryl glucosides or salts thereof as disclosed in U.S. Pat. No. 6,683,056 (the disclosure of which is incorporated herein by reference in its entirety) as follows:

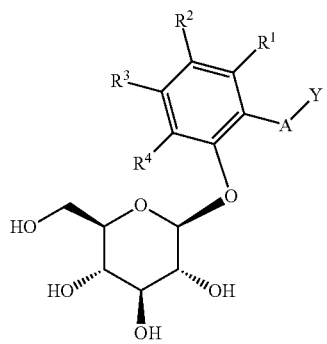

XIX wherein
when Y is

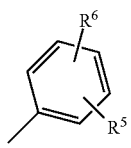

or heteroaryl;

$R^1$, $R^2$, $R^3$, and $R^4$ are the same or different and are independently selected from hydrogen, OH, $OR^7$, lower alkyl, or halogen, or two of $R^1$, $R^2$, $R^3$, and $R^4$ together with the carbons to which they are attached can form an annelated five-, six- or seven-membered carbocycle or heterocycle which may contain 1 to 4 heteroatoms in the ring which are N, O, S, SO, and/or $SO_2$;

$R^5$ and $R^6$ are the same or different and are independently selected from hydrogen, OH, $OR^{7a}$, $-$OAryl, $-OCH_2$Aryl, lower alkyl, cycloalkyl, aryl, arylalkyl, $CF_3$, arylalkenyl, $-OCHF_2$, $-OCF_3$, halogen, $-CN$, $-CO_2R^{7b}$, $-CO_2H$, $COR^{8f}$, $CHOHR^{8g}$, $CH(OR^{7h})R^{8h}$, $-CONR^8R^{8a}$, $-NHCOR^{7c}$, $-NHSO_2R^{7d}$, $-NHSO_2$Aryl, $-SR^{7e}$, $-SOR^{7f}$, $-SO_2R^{7g}$, $-SO_2$Aryl, $-OCH_2CO_2R^{7i}$, $-OCH_2CO_2H$, $-OCH_2CONR^{8b}R^{8c}$, $-OCH_2CH_2NR^{8d}R^{8e}$, or a five-, six- or seven-membered heterocycle which may contain 1 to 4 heteroatoms in the ring which are N, O, S, SO, and/or $SO_2$, or $R^5$ and $R^6$ together with the carbons to which they are attached form an annelated five-, six- or seven-membered carbocycle or heterocycle which may contain 1 to 4 heteroatoms in the ring which are N, O, S, SO, and/or $SO_2$;

$R^7$, $R^{7a}$, $R^{7b}$, $R^{7c}$, $R^{7d}$, $R^{7e}$, $R^{7f}$, $R^{7g}$, $R^{7h}$, and $R^{7i}$ are independently lower alkyl;

$R^8$, $R^{8a}$, $R^{8b}$, $R^{8c}$, $R^{8d}$, $R^{8e}$, $R^{8f}$, $R^{8g}$, and $R^{8h}$ are the same or different and are independently selected from hydrogen, alkyl, aryl, arylalkyl, cycloalkyl, or together with the nitrogen to which they are attached form an annelated five-, six- or seven-membered heterocycle which may contain 1 to 4 heteroatoms in the ring which are N, O, S, SO, and/or $SO_2$; and A is $O(CH_2)_m$, S, $NH(CH_2)_m$, or $(CH_2)_n$ where n is 0-3 and m is 0-2.

Other O-aryl glucosides SGLT2 inhibitors which may be used in the invention are disclosed in the following references all of which are incorporated herein by reference.

1) EP 598359A1 (also JP 035988) (and any U.S. counterpart applications) (Tanabe Seiyaku) discloses compounds of the following structure

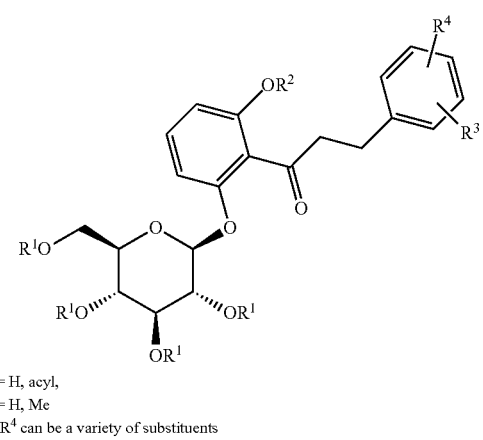

XX $R^1$ = H, acyl,
$R^2$ = H, Me
$R^3$, $R^4$ can be a variety of substituents

2) EP 0850948A1 (and any U.S. counterpart applications) discloses the following structures of genus

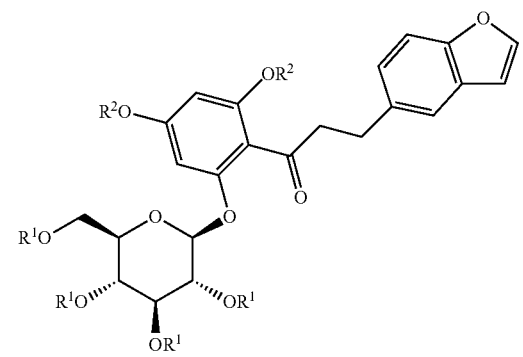

XXI $R^1$ = H, acyl, CO(OAlkyl)
$R^2$ = H, allyl
$R^3$ = H or Me

3) JP 09188625A (and any U.S. counterpart applications) expands upon structure XXI (of EP 0850948A1) to include examples of XXI where $R^3$ is H and where the five-membered ring is saturated as well as the counterparts of benzothiophenes (O=S) and indenes (O=CH_2). EP 684254-A1 appears to encompass derivatives of structure XXI disclosed in JP 09188625A.

XXII

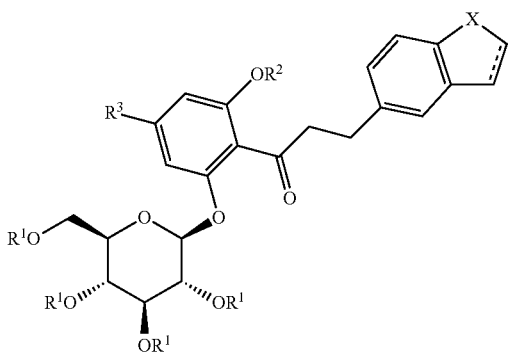

R¹ = H, acyl, CO(OAlkyl)
R² = H, allyl
R³ = H

4) JP 09124685A (and any U.S. counterpart applications) expands upon structure XXI for R³=H to include derivatives of mono acylated C6 hydroxyl where the acyl group is a substituted benzoic or pyridyl carboxylic acid or a urethane generated from the corresponding phenol.

XXIII

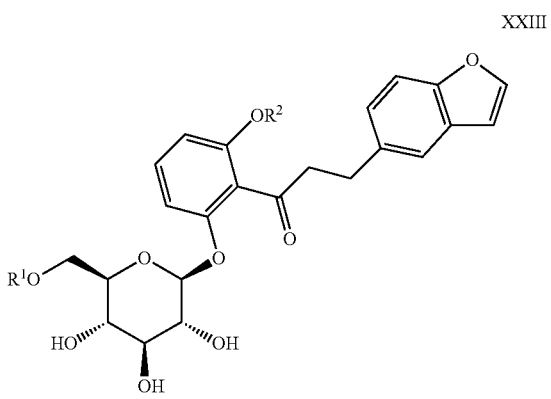

R¹ = H, CO-aryl, CO(OAryl)
R² = H

5) JP 09124684 (and any U.S. counterpart applications) discloses derivatives of structure XXI

XXIV

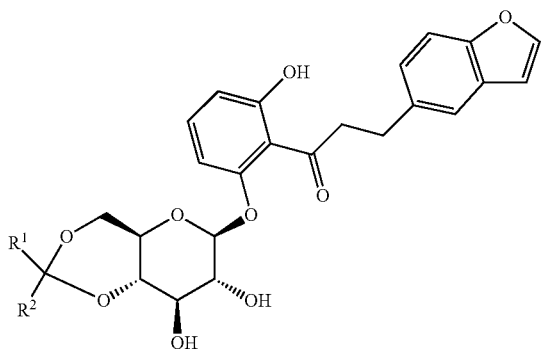

R¹, R² = H, alkyl, alkoxy, aryl or together oxo

6) EP 773226-A1 (and any U.S. counterpart applications) discloses derivatives of structure XXI

XXV

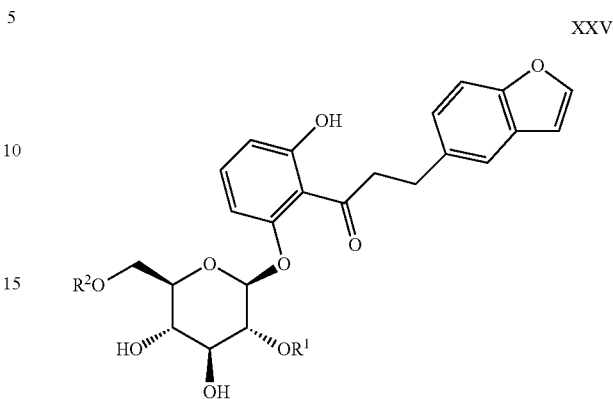

R¹ = alkanoyl if R² = H
R² = alkoxycarbonyl if R¹ = H

7) JP 08027006-A (and any U.S. counterpart applications) discloses derivatives of structure XX where various combinations of the glucose hydroxyl are acylated and appears to be similar to EP 598359A1.

8) EP 684254-A1 (and any U.S. counterpart applications) appears to encompass derivatives of structure XXI disclosed in JP 09188625A.

Other disclosures and publications which disclose SGLT2 inhibitors that can be employed according to the methods of the invention are as follows:

9) K. Tsujihara et al., *Chem. Pharm. Bull.*, 44:1174-1180 (1996);

10) M. Hongu et al., *Chem. Pharm. Bull.*, 46:22-33 (1998);

11) M. Hongu et al., *Chem. Pharm. Bull.*, 46:1545-1555 (1998); and

12) A. Oku et al., *Diabetes*, 48:1794-1800 (1999).

13) JP 10245391 (Dainippon) discloses 500 structures as hypoglycemic agents for treatment of diabetes. These are O-glucosides of hydroxylated coumarins.

In addition to the above SGLT2 inhibitors, other SGLT2 inhibitors that can be employed using the methods disclosed herein include those disclosed in US 2005/0233982 (Boehringer Ingelheim Corp.), US 2005/0119192 (Kissei Pharmaceutical Co.), WO 2006/035796 (Kissei Pharmaceutical Co.), JP 2006/117651 (Taisho Pharmaceutical Co.), JP 2004/4359630 (Yamanouchi Pharmaceutical Co.), WO 2006/080421 (Chugai Seiyaku Kabushiki Kaishi), US 2005/0233988 (Tanabe Seiyaku Co.), WO 2005/012321 (Tanabe Seiyaku Co.), U.S. Pat. No. 7,015,201 (Ajinomoto Co.), WO 2006/058597 (Merck Patent GmbH), WO 2006/011469 (Chugai Seiyaku Kabushiki Kaisha), US 2003/0195235 (Johnson & Johnson), and WO 2006/037537 (Boehringer Ingelheim).

Preferred SGLT2 inhibitors for use in the methods and compositions of the invention include compound I, compound II, and compound MA:

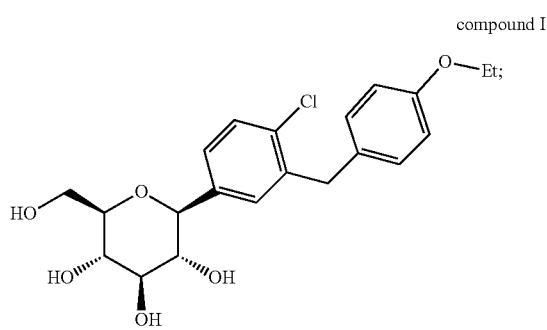 [SMILES: CCOc1ccc(Cc2cc([C@@H]3O[C@H](CO)[C@@H](O)[C@H](O)[C@H]3O)ccc2Cl)cc1]

compound I or pharmaceutically acceptable salts thereof, all stereoisomers thereof, or a prodrug ester thereof;

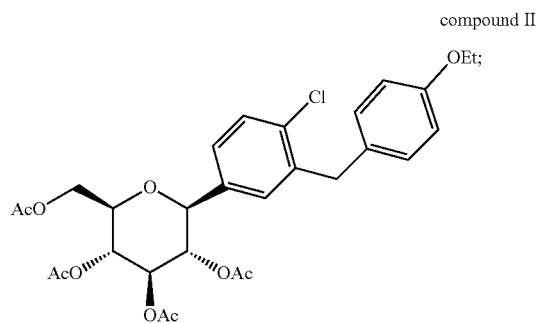 [SMILES: CCOc1ccc(Cc2cc([C@@H]3O[C@H](COC(C)=O)[C@@H](OC(C)=O)[C@H](OC(C)=O)[C@H]3OC(C)=O)ccc2Cl)cc1]

compound II or pharmaceutically-acceptable salts thereof, all stereoisomers thereof, or prodrug esters thereof;

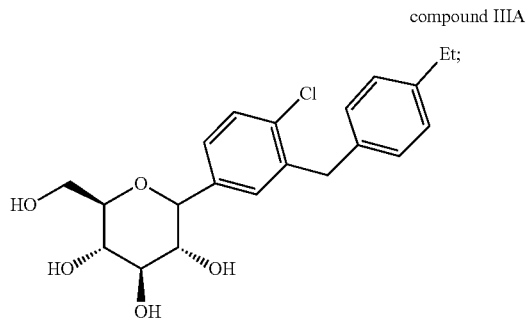 [SMILES: CCc1ccc(Cc2cc(C3O[C@H](CO)[C@@H](O)[C@H](O)[C@H]3O)ccc2Cl)cc1]

compound IIIA or a pharmaceutically acceptable salts thereof, all stereoisomers thereof, or a prodrug ester thereof.

Also preferred are crystalline forms of compound I above including the crystalline forms disclosed in US published patent application US/2008/0004335, the disclosures of which are incorporated herein by reference in their entirety for any purpose. A most preferred crystalline form of compound I is the (S) propylene glycol solvate or hydrate, compound Ia or dapagliflozin-PGS, shown below. It is to be understood the (R) propylene glycol solvate or hydrate is also a preferred compound for use in the methods and compositions of the invention.

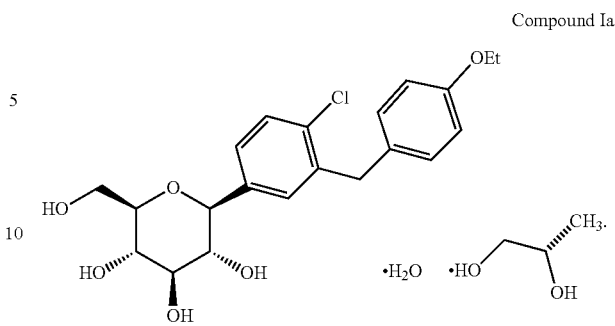

Compound Ia

The crystalline structure of compound Ia is characterized by one or more of the following:

a) unit cell parameters substantially equal to the following:

Cell Dimensions:

a=11.2688(8) Å b=4.8093(3) Å c=46.723(3) Å

α=90 degrees

β=90 degrees

γ=90 degrees

Space group=$P2_12_12_1$

Molecules/asymmetric unit=1 wherein measurement of said crystalline structure is at room temperature and which is characterized by fractional atomic coordinates substantially as listed in Table 4 of U.S. Provisional Application No. 60/817,118;

b) a powder x-ray diffraction pattern comprising 2θ values (CuKα γ=1.5418 Å) selected from the group consisting of 3.8±0.1, 7.6±0.1, 8.1±0.1, 8.7±0.1, 15.2±0.1, 15.7.4±0.1, 17.1±0.1, 18.9±0.1 and 20.1±0.1, at room temperature;

c) a solid state $^{13}$C NMR spectrum having substantially similar peak positions at 16.2, 17.6, 39.3, 60.9, 63.3, 69.8, 76.9, 78.7, 79.4, 113.8, 123.6, 129.3, 130.5, 132.0, 135.7, 139.1 and 158.0 ppm, as determined on a 400 MHz spectrometer relative to TMS at zero;

d) a differential scanning calorimetry thermogram having an endotherm in the range of about 50° C. to 78° C. or as shown in FIG. 7 of U.S. Provisional Application No. 60/817,118;

e) thermal gravimetric analysis curve with about 18.7% weight loss from about room temperature up to about 240° C. or as shown in FIG. 5 of U.S. Provisional Application No. 60/817,118; or f) having a proton NMR having substantially similar peak positions as listed in Table 1A of U.S. Provisional Application No. 60/817,118.

A process for the preparation of compound Ia is provided in US/2008/0004335. Generally, compound II (prepared as described in PCT/US03/041373, Examples 17-19) is treated with aqueous base, such as aqueous sodium hydroxide, in an alcohol solvent, such as methanol, preferably under an inert atmosphere, such as nitrogen, at an elevated temperature (between about 5° C. and 85 C) to form compound I

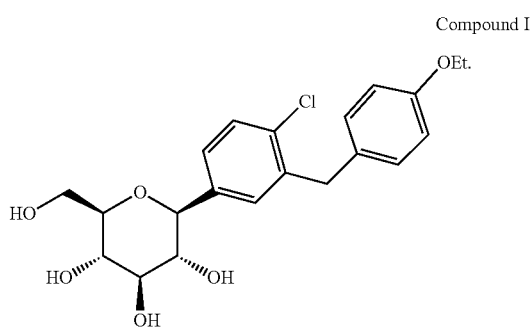 [SMILES: CCOc1ccc(Cc2cc([C@@H]3O[C@H](CO)[C@@H](O)[C@H](O)[C@H]3O)ccc2Cl)cc1]

Compound I

The reaction mixture containing compound I is treated with an organic solvent such as methyl tert-butyl ether or an alkyl acetate such as ethyl acetate, methyl acetate, isopropyl acetate, or butyl acetate, and (S)-propylene glycol, optionally adding seeds of compound Ia to the mixture, to provide compound Ia.

The SGLT2 inhibitor employed in accordance with the invention can be administered to various mammalian species, such as dogs, cats, humans, etc., in need of treatment. These agents can be administered systemically, such as orally or parenterally.

The SGLT-2 inhibitor can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered containing amounts of SGLT-2 inhibitor of from about 1 to about 1000 mg per day preferably from about 2 to about 400 mg per day, in single or divided doses of one to four times daily.

Cytotoxic agents which may be employed in conjunction with the SGLT-2 inhibitors, in accordance with the invention, may be administered in the same or different dosage forms with the SGLT2 inhibitor.

Cytotoxic agents approved by the FDA such as those listed in the Physicians' Desk Reference, 61$^{st}$ Ed. (2007), which may be employed include doxorubicin, doxorubicin valerate, idarubicin HCl, mitomycin, paclitaxel, taxotere, teniposide, etoposide, carboplatin, busulfan, megestrol acetate, mitotane, altretamine, lomustine, carmustine, estramustine phosphate sodium, procarbazine hydrochloride, cytarabine, dasatinib, gemcitabine, as well as an apoptosis agonist, DNA topoisomerase inhibitors, microtubule stimulants, beta tubulin antagonists, tubulin antagonist and microtubule inhibitors, thymidylate synthase inhibitors, DNA antagonists, ErbB inhibitors, angiogenesis inhibitors, DNA topoisomerase ATP hydrolyzing inhibitors, DNA antagonists, endothelial growth factor receptor kinase inhibitors, p21 stimulants, endothelial growth factor receptor kinase inhibitors, p21 stimulants, microtubule inhibitors, dihydrofolate reductase inhibitors, such as ATP-binding cassette, subfamily B (MDR/TAP), member 1, Caspase 3, colony stimulating factor 2, thymidylate synthetase, topoisomerase (DNA) I, tubuline beta polypeptide, Cyclin G1, Cyclin-dependent kinase inhibitor 1A, kinase insert domain receptor (a type III receptor tyrosine kinase), mucin 1 transmembrane, DNA (cytosine-5-)-methyltransferase 1, epidermal growth factor receptor, and eukaryotic translation elongation factor 1 alpha 1, as well as 9-methoxyellipticine, and N-methylellipticinium,

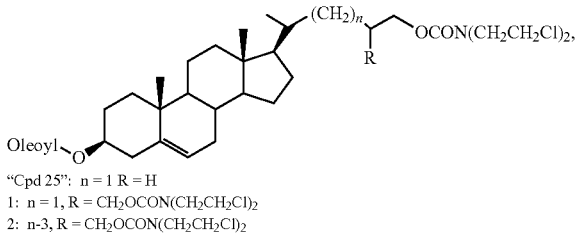

"Cpd 25": n = 1 R = H
1: n = 1, R = CH$_2$OCON(CH$_2$CH$_2$Cl)$_2$
2: n-3, R = CH$_2$OCON(CH$_2$CH$_2$Cl)$_2$ prednimustine, WB4291 (1-[bis(2-chloroethyl)amino]-3-methylnaphthalene), daunomycin and vincristine.

Preferred cytotoxic agents to be employed herein will depend upon the particularly neoplastic disease to be treated.

The various cytotoxic agents described above may be employed in dosages and regimens as generally known in the art or in the PHYSICIANS' DESK REFERENCE (PDR) or REMINGTON'S PHARMACEUTICAL SCIENCES (Mack Publishing Co., Easton, Pa.).

Unless otherwise indicated, the dosages and formulations for the SGLT2 inhibitor will be disclosed in the various patents and applications discussed above.

The various formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tabletting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also include a coating layer which may comprise from 0 to about 15% by weight of the tablet composition. The coating layer may comprise any conventional coating formulations and will include one or more film-formers or binders, such as a hydrophilic polymer like hydroxypropylmethylcellulose, and/or a hydrophobic polymer like methacrylic acid esters neutral polymer, ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

It will be recognized by one of skill in the art that the amount of drug required for therapeutic effect on administration will, of course, vary with the agent chosen, the nature and severity of the condition and the mammal undergoing treatment, and is ultimately at the discretion of the physician. Furthermore, the optimal quantity and spacing of individual dosages of a drug will be determined by the nature and extent of the weight loss desired, the form, route and site of administration, the particular patient being treated and that such optima can be determined by conventional techniques. It will also be appreciated that the optimal course of treatment, this is, the number of doses given, can be ascertained by those skilled in the art using conventional course of treatment determination tests.

An example of a preferred formulation containing an SGLT2 inhibitor for use herein and a process for preparing such formulation are set out in U.S. Provisional Application Ser. No. 60/896,286 filed Mar. 22, 2007, the disclosure of which is incorporated herein by reference in its entirety for any purpose.

Preferred tablet formulations in accordance with the invention are set out below.

| Material Tablet | Range %/mg by weight of 200 mg tablet | Preferred Range %/mg by weight of 200 mg tablet |
|---|---|---|
| Dapagliflozin | 0.1 to 70%/0.2 to 140 mg | 1 to 50%/2 to 100 mg |
| Bulking Agent | 2 to 95%/4 to 190 mg | 10 to 85%/20 to 170 mg |
| Lactose | 0 to 95%/0 to 190 mg | 20 to 75%/10 to 100 mg |
| Microcrystalline cellulose | 0 to 95%/0 to 190 mg | 20 to 75%/40 to 150 mg |
| Disintegrant | 0 to 20%/0 to 40 mg | 0.25 to 10%/0.5 to 20 mg |
| Croscarmellose sodium | 0 to 20%/0 to 40 mg | 2 to 10%/4 to 20 mg |
| Crospovidone | 4 to 12%/4 to 20 mg | 6 to 10%/12 to 20 mg |
| Lubricant | 0.1 to 5%/0.2 to 10 mg | 0.2 to 2%/0.4 to 4 mg |
| Magnesium Stearate | 0.1 to 5%/0.2 to 10 mg | 0.2 to 2%/0.4 to 4 mg |
| Anti adherent/glidant Talc, silicon dioxide | 0 to 20%/0 to 40 mg | 1 to 4%/2 to 8 mg |

| Outer Protective Coating Layer | %/mg by weight of 200 mg tablet | %/mg by weight of 200 mg tablet |
|---|---|---|
| Coating polymer, and optional plasticizer, glidants and color | 0.5 to 50%/1 to 100 mg | 1 to 5%/2 to 10 mg |

Preferred stock granulation formulations (for use in capsules) in accordance with the invention are set out below.

| Material Tablet | Range %/mg by weight of 200 mg tablet | Preferred Range %/mg by weight of 200 mg tablet |
|---|---|---|
| Dapagliflozin | 0.1 to 70%/0.2 to 140 mg | 1 to 50%/2 to 100 mg |
| Bulking Agent/Binder | 2 to 95%/4 to 190 mg | 10 to 85%/20 to 170 mg |
| Microcrystalline cellulose | 1 to 95%/1 to 190 mg | 20 to 75%/10 to 100 mg |
| Pregelatinized starch | 0 to 95%/0 to 190 mg | 20 to 75%/40 to 150 mg |
| Disintegrant | 0 to 20%/0 to 40 mg | 0.25 to 10%/0.5 to 20 mg |
| Sodium Starch glycolate | 0 to 20%/0 to 40 mg | 2 to 10%/4 to 20 mg |
| Lubricant | 0.1 to 5%/0.2 to 10 mg | 0.2 to 2%/0.4 to 4 mg |
| Magnesium Stearate | 0.1 to 5%/0.2 to 10 mg | 0.2 to 2%/0.4 to 4 mg |
| Anti adherent/glidant Talc silicon dioxide | 0 to 20%/0 to 40 mg | 1 to 4%/2 to 8 mg |

The pharmaceutical formulation for use in the method of the invention in the form of a tablet or capsule may be obtained by a process which includes the steps of:

a) formulating granules by wet granulation of the SGLT2 inhibitor,
b) blending the granules with a tabletting aid and diluent,
c) tabletting the blend thus obtained into tablets, or
d) loading the granules into capsules.

The mixture used for forming the granules includes a granulating binder. The granulating binder is preferably a polyvinylpyrrolidone such as, for example, a polyvinylpyrrolidone having a molecular weight of 45,000. The polyvinylpyrrolidone may be used in a proportion of 2 to 4% by weight with respect to the final tablet.

After the granulating step, the granules may be sieved and dried.

The granules are then blended with a diluent and tabletting aid. The diluent may be a conventional filler usually used for making tablets, such as microcrystalline cellulose. The tabletting aid may be a conventional material, such as magnesium stearate.

A typical injectable preparation is produced by aseptically placing 50 mg of compounds of structure I into a vial, aseptically freeze-drying and sealing. For use, the contents of the vial are mixed with 2 mL of physiological saline, to produce an injectable preparation.

SGLT2 inhibitor activity of the compounds of the invention may be determined by use of an assay system as set out below.

Assay for SGLT2 Activity

The mRNA sequence for human SGLT2 (GenBank No. M95549) was cloned by reverse-transcription and amplification from human kidney mRNA, using standard molecular biology techniques. The cDNA sequence was stably transfected into CHO cells, and clones were assayed for SGLT2 activity essentially as described in Ryan et al. (1994) (cited below). Evaluation of inhibition of SGLT2 activity in a clonally selected cell line was performed essentially as described in Ryan et al., with the following modifications. Cells were grown in 96-well plates for 2-4 days to 75,000 or 30,000 cells per well in F-12 nutrient mixture (Ham's F-12), 10% fetal bovine serum, 300 ug/ml Geneticin and penicillin-streptomycin. At confluence, cells were washed twice with 10 mM Hepes/Tris, pH 7.4, 137 mM N-methyl-D-glucamine, 5.4 mM KCl, 2.8 mM CaCl$_2$, 1.2 mM MgSO$_4$. Cells then were incubated with 10 μM [$^{14}$C]AMG, and 10 μM inhibitor (final DMSO=0.5%) in 10 mM Hepes/Tris, pH 7.4, 137 mM NaCl, 5.4 mM KCl, 2.8 mM CaCl$_2$, 1.2 mM MgSO$_4$ at 37° C. for 1.5 hr. Uptake assays were quenched with ice cold 1×PBS containing 0.5 mM phlorizin, and cells were then lysed with 0.1% NaOH. After addition of MicroScint scintillation fluid, the cells were allowed to shake for 1 hour, and then [$^{14}$C] AMG was quantitated on a TopCount scintillation counter. Controls were performed with and without NaCl. For determination of EC$_{50}$ values, 10 inhibitor concentrations were used over 2 log intervals in the appropriate response range, and triplicate plates were averaged across plates. Ryan, M. J., Johnson, G., Kirk, J., Fuerstenberg, S. M., Zager, R. A. and Torok-Storb, B., "HK-2: an immortalized proximal tubule epithelial cell line from normal adult human kidney", *Kidney International*, 45:48-57 (1994).

EXAMPLES

The following working Examples are illustrative of the invention. All temperatures are expressed in degrees Centigrade unless otherwise indicated.

Examples 1 to 3

Capsules containing compound I were prepared in strengths of 2.5 mg (Example 1), 10 mg (Example 2) and 100 mg (Example 3) as two-piece, gray opaque size #0 (2.5 mg and 10 mg) and size #00 (for 0 mg) hard gelatin capsules.

Examples 1 and 2

Composition: 25.0 mg of Granulation containing compound I for Capsules (10.0% w/was the non-solvated form), filled in Gray, Opaque, Size #0 Capsule Shell.

A. Stock Granulation Composition

| Ingredient | Amount (% w/w) |
| --- | --- |
| Compound I[1] | 10.0 |
| Pregelatinized Starch, NF | 15.0 |
| Microcrystalline Cellulose, NF[2] | 68.75 |
| Sodium Starch Glycolate, NF | 3.0 |
| Silicon Dioxide, NF | 2.0 |
| Magnesium Stearate, NF[3] | 1.25 |

[1]This amount is expressed in terms of the amount of compound I at 100% purity. The exact amount will vary depending on the purity of compound I.
[2]The amount of microcrystalline cellulose used will vary depending on the purity of compound I.
[3]The preferred amount is 1.25% (w/w). The range is 1.25-1.50% (w/w).

The stock granulation of Part A and the Example 1 and Example 2 capsules were prepared according to the following procedures.

Example 1

B. Example 1 Stock Granulation Procedure

1. Screen compound I.
2. Screen silicon dioxide.
3. Mix silicon dioxide with compound I in a suitable blender.
4. Screen pregelatinized starch and microcrystalline cellulose, if necessary.
5. Add ingredients from Step 4 to a suitable blender.
6. Add mixture from Step 3 to the blend from Step 5, and mix.
7. Screen sodium starch glycolate.
8. Add ingredient from Step 7 to the blend from Step 6, and mix.
9. Screen the blend from Step 8, and mix.
10. Screen portion of magnesium stearate.
11. Add ingredient from Step 10 to the blend from Step 9, and mix.
12. Densify the blend from Step 11.
13. Reduce the densified blend Step 12.
14. Screen the remaining portion of magnesium stearate.
15. Add ingredient from Step 14 to the granulation from Step 13, and mix.

C. Example 1 Product

Compound I Capsule, 2.5 mg (As the Non-Solvated Form)

1. Fill empty capsule shells with sufficient Example 1 Part A stock granulation for capsules (10.0%) w/w (as the non-solvated form), to provide 2.5 mg capsules.
2. De-dust the capsules.

Example 2

Product

Compound I Capsule, 10 mg (As the Non-Solvated Form)

1. Fill empty capsule shells with Example 1 Part A stock granulation for capsules (10.0% w/w as the non-solvated form), to provide 10 mg capsules.
2. De-dust the capsules.
3. Weight sort the capsules.

The Example 1 (2.5 mg) and Example 2 (10 mg) capsules are used in treating obesity.

Example 3

Compound I Capsule, 100 mg

Composition: 438.6 mg of compound I (Example 3 Part A) Stock Granulation for Capsules (22.8% w/w as the non-solvated form), filled in Gray, Opaque, Size #0 Capsule Shell.

A. Stock Granulation Composition

| Ingredient | Amount (% w/w) |
|---|---|
| Compound I[1] | 22.8 |
| Pregelatinized Starch, NF | 15.0 |
| Microcrystalline Cellulose, NF[2] | 55.95 |
| Sodium Starch Glycolate, NF | 3.0 |
| Silicon Dioxide, NF | 2.0 |
| Magnesium Stearate, NF[3] | 1.25 |

[1]This amount is expressed in terms of the amount of compound I at 100% purity. The exact amount will vary depending on the purity of compound I.
[2]The amount of microcrystalline cellulose used will vary depending on the purity of compound I.
[3]The preferred amount is 1.25% (w/w). The range is 1.25-1.50% (w/w).

The stock granulation of Part A and the Example 3 capsules were prepared according to the following procedures.

B. Stock Granulation Procedure

1. Screen silicon dioxide.
2. Mix silicon dioxide with compound I in a suitable blender.
3. Screen the blend from Step 2, and mix again.
4. Screen pregelatinized starch and microcrystalline cellulose, if necessary.
5. Add ingredients form Step 4 to the blend from Step 3, and mix.
6. Screen sodium starch glycolate.
7. Add ingredient from Step 6 to the blend from Step 5, and mix.
8. Screen a portion of magnesium stearate.
9. Add ingredient from Step 8 to the blend from Step 7, and mix.
10. Densify the blend from Step 9.
11. Reduce the densified blend from Step 10.
12. Screen the remaining portion of magnesium stearate.
13. Add ingredient from Step 12 to the granulation from Step 11, and mix.

C. Example 3 Product: Compound I Capsule, 100 mg (As the Non-Solvated Form)

1. Fill empty capsule shells with Example 3 stock granulation for capsules (22.8% w/w as the non-solvated form).
2. De-dust the capsules.
3. Weight sort the capsules.

The so-formed capsules of Example 1 (2.5 mg), Example 2 (10 mg) and Example 3 (100 mg) are used to inhibit or prevent rejection of renal transplant rejection.

Examples 4 to 6

Tablets containing the SGLT2 inhibitor compound Ia (the (S) propylene glycol solvate or (S) propylene glycol hydrate of compound I) were prepared in strengths of 2.5 mg (Example 4), 10 mg (Example 5) and 50 mg (Example 6) as described below.

Example 4

Product

Compound Ia Tablet, 2.5 mg

A. Tablet Composition

| Ingredient | Amount |
|---|---|
| Compound Ia[1] | 3.075 mg |
| Microcrystalline Cellulose, NF[2] | 67.113 mg |
| Lactose Anhydrous, NF | 25.000 mg |
| Crospovidone, NF | 8.750 mg |
| Croscarmellose Sodium, NF | 3.750 mg |
| Talc, USP | 12.500 mg |
| Silicon Dioxide, NF | 2.875 mg |
| Magnesium Stearate, NF[3] | 1.938 mg |

[1]Compound Ia is a propylene glycol solvate. The amount of non-solvated compound I is theoretically equivalent to 81.29% of compound Ia. The actual amount of compound Ia will depend on the "As Is" purity of the drug.
[2]This is the compensating excipient. The amount used may vary depending on the "As Is" purity of the drug and/or the actual amount of magnesium stearate used.
[3]The target amount is 1.94 mg. Acceptable range is 1.55-2.33 mg.

The stock granulation of Part A and the Example 4 tablets were prepared according to the following procedures.

B. Stock Granulation Procedure

1. Deaggregate compound Ia and magnesium stearate separately using a suitable screen.
2. Mix compound Ia with a portion of microcrystalline cellulose in a suitable mixer and transfer it into a suitable blender.
3. "Dry Rinse" the mixer used for mixing Step 2 with a portion of microcrystalline cellulose.
4. Add the blend from Step 3 to the blend from Step 2.
5. Mix the mixture from Step 4 with remaining microcrystalline cellulose, portion of crospovidone, portion of croscarmellose sodium, portion of silicon dioxide and lactose anhydrous.
6. Add talc and intragranular magnesium stearate to the mixture from Step 5 and mix.
7. Compact the powder blend from Step 6.
8. Reduce compact from Step 7 to form granules.
9. Mix the granules from Step 8 with remaining amounts of crospovidone, croscarmellose sodium and silicon dioxide.
10. Mix the granules from Step 9 with remaining amount of magnesium stearate.

C. Example 4 Product: Compound Ia Tablet, 2.5 mg

1. Setup the tabletting equipment.
2. Compress the Example 4 stock granulation into tablets (2.46% w/w), (2.5 mg).

Example 5

Product

Compound Ia Tablet, 10 mg

A. Tablet Composition

| Ingredient | Amount |
|---|---|
| Compound Ia[1] | 12.300 mg |
| Microcrystalline Cellulose, NF[2] | 57.888 mg |
| Lactose Anhydrous, NF | 25.000 mg |
| Crospovidone, NF | 8.750 mg |

-continued

| Ingredient | Amount |
| --- | --- |
| Croscarmellose Sodium, NF | 3.750 mg |
| Talc, USP | 12.500 mg |
| Silicon Dioxide, NF | 2.875 mg |
| Magnesium Stearate, NF[3] | 1.938 mg |

[1]Compound Ia is a propylene glycol solvate. The amount of non-solvated compound Ia is theoretically equivalent to 81.29% of compound Ia. The actual amount of compound Ia will depend on the "As Is" purity of the drug.
[2]This is the compensating excipient. The amount used may vary depending on the "As Is" purity of the drug and/or the actual amount of magnesium stearate used.
[3]The target amount is 1.94 mg. Acceptable range is 1.55-2.33 mg.

The stock granulation of Part A and the Example 5 tablets were prepared according to the following procedures.

B. Stock Granulation Procedure

1. Deaggregate compound Ia and magnesium stearate separately using a suitable screen.
2. Mix microcrystalline cellulose, compound Ia portion of crospovidone, portion of croscarmellose sodium, portion of silicon dioxide and lactose anhydrous in a suitable blender.
3. Add talc and intragranular magnesium stearate to the mixture from Step 2 and mix in a suitable blender.
4. Compact the powder blend from Step 3.
5. Reduce compact from Step 4 to form granules.
6. Mix the granules from Step 5 with remaining amounts of crospovidone, croscarmellose sodium and silicon dioxide.
7. Mix the granules from Step 6 with remaining amount of magnesium stearate.

C. Example 5 Product: Compound Ia Tablet, 10 mg
1. Setup the tabletting equipment.
2. Compress the Example 5 stock granulation into tablets (9.84% w/w).

Example 6

Product

Compound Ia Tablet, 50 mg

A. Tablet Composition

| Ingredient | Amount |
| --- | --- |
| Compound Ia[1] | 61.660 mg |
| Microcrystalline Cellulose, NF[2] | 114.090 mg |
| Lactose Anhydrous, NF | 62.600 mg |
| Crospovidone, NF | 21.910 mg |
| Croscarmellose Sodium, NF | 9.390 mg |
| Talc, USP | 31.300 mg |
| Silicon Dioxide, NF | 7.200 mg |
| Magnesium Stearate, NF[3] | 4.850 mg |

[1]The amount shown is based on the amount of compound Ia at 100% purity. The exact amount may vary depending on the "As Is" purity of compound Ia.
[2]This is the compensating excipient. The amount used may vary depending on the "As Is" purity of the drug and/or the actual amount of magnesium stearate used.
[3]The target amount is 4.85 mg. Acceptable range is 3.76-5.95 mg.

The stock granulation of Part A and the Example 6 tablets were prepared according to the following procedures.

B. Stock Granulation Procedure

1. Mix compound Ia microcrystalline cellulose, lactose anhydrous, crospovidone, croscarmellose sodium, talc and silicon dioxide in a suitable blender.
2. Pass the mixture from Step 1 through a suitable mill.
3. Determine the yield from Step 1 and calculate the amount of magnesium stearate required.
4. Mix the mixture from Step 2 in a suitable blender.
5. Mix the mixture from Step 4 with magnesium stearate.
6. Dry granulate the powder blend from Step 5.
7. Size the granulation from Step 6.
8. Determine the yield based on Step 7.
9. Mix the granules from Step 8 with remaining amount of crospovidone, croscarmellose sodium and silicon dioxide.
10. Mix the granules from Step 9 with remaining amount of magnesium stearate.

C. Example 6 Product: Compound Ia PGS Tablet, 50 mg
1. Setup the tabletting equipment.
2. Compress the Example 6 stock granulation (19.7% w/w), into tablets (50 mg).

The so-formed tablets of Example 4 (2.5 mg), Example 5 (10 mg) and Example 6 (50 mg) are used to inhibit or prevent rejection of renal transplant rejection.

Example 7

An oral solution (0.5 mg/mL) was prepared by dissolving compound I in a mixture of polyethylene glycol 400, NF and water for injection, USP or purified water (30:70% v/v). The oral solution was clear and colorless. It is used to inhibit or prevent renal transplant rejection.

Example 8

Figure 2:
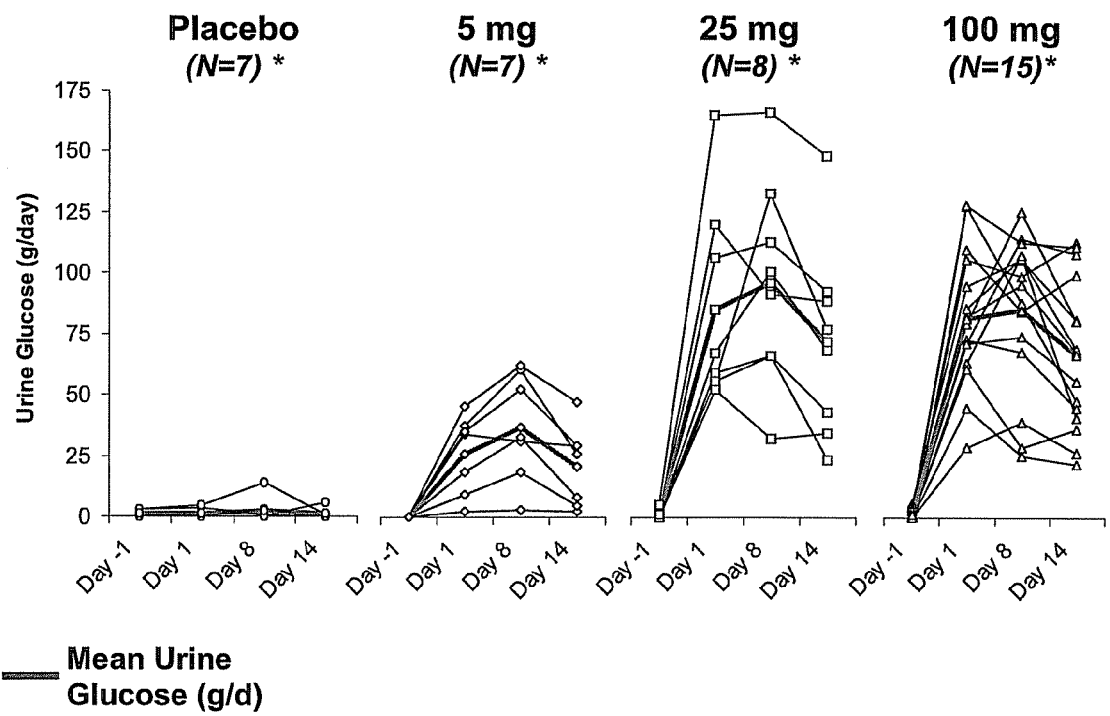
FIG. 2 depicts a series of graphs showing urine glucose excretion in diabetic subjects treated with Compound Ia and placebo.

The glucosuric effects of compound Ia results in significant loss of calories in the urine versus a known SGLT2 inhibitor (GSK 869,682). Thus, as seen in FIG. 1, the results of an indirect comparison of two single ascending dose studies of SGLT2 inhibitors is shown. The panel at the top of FIG. 1 is from a presentation by GSK in an analyst meeting, showing the amount of glucose excretion/day in healthy subjects taking 50, 100, 200 or 500 mg of GSK 869,682. The panel at the bottom is from study MB-102001, showing the amount of glucose excretion/day in healthy subjects taking 5, 20, 50 or 100 mg of compound Ia. This is further confirmed in a 14-day multiple ascending dose phase 2a study in subjects with type 2 diabetes. Results from the 24-hour glucose excretion are shown in FIG. 2 for all subjects in the MB-102003 study. The mean urine glucose is in the darker lines. Compared to subjects on placebo, who had low urine glucose excretion, subjects randomized to compound Ia had higher urine glucose excretion.

What is claimed is:

1. A method for treating cancers that express SGLT2 levels higher than normal cells in a mammal comprising administering to the mammal in need of such treatment a therapeutically effective amount of an SGLT2 inhibitor having the structure

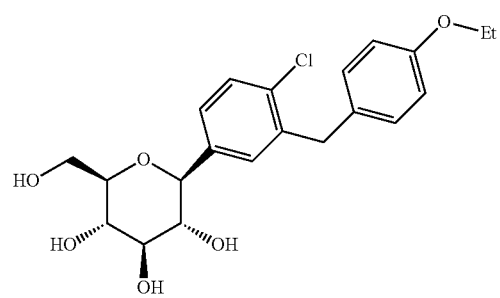 [SMILES: CCOc1ccc(Cc2cc([C@@H]3O[C@H](CO)[C@@H](O)[C@H](O)[C@H]3O)ccc2Cl)cc1]

or a prodrug ester thereof, or a pharmaceutically acceptable salt thereof.

2. The method according to claim 1 wherein the mammal is a human.

3. The method according to claim 2 wherein the cancer is lung cancer metastatic lesions.

4. The method according to claim 2 wherein the cancer is lung cancer metastatic lesions of the liver.

5. The method according to claim 2 wherein the cancer is lung cancer metastatic lesions of the lymph nodes.

6. The method according to claim 1 wherein the SGLT2 inhibitor has the structure

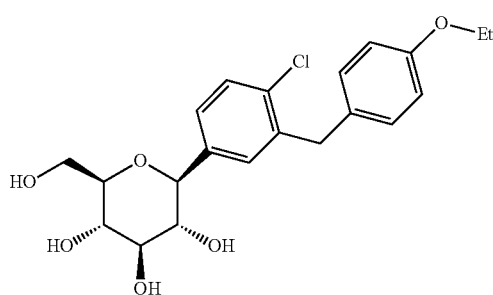 [SMILES: CCOc1ccc(Cc2cc([C@@H]3O[C@H](CO)[C@@H](O)[C@H](O)[C@H]3O)ccc2Cl)cc1]

Compound Ia

7. A method for treating cancers that express SGLT2 levels higher than normal cells in a mammal comprising administering to the mammal in need of such treatment a therapeutically effective amount of a pharmaceutical composition comprising an SGLT2 inhibitor having the structure

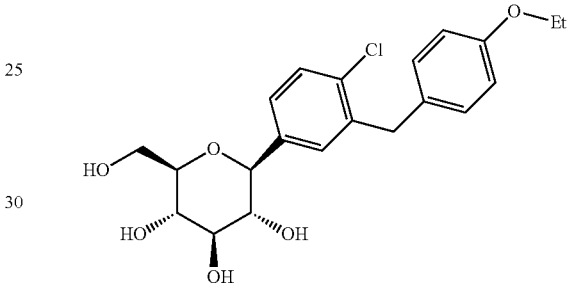

o or a prodrug ester thereof, or a pharmaceutically acceptable salt thereof and at least one pharmaceutically acceptable carrier, excipient, or diluent.

8. The method according to claim 7 wherein the mammal is a human.

9. The method according to claim 8 wherein the cancer is lung cancer metastatic lesions.

10. The method according to claim 8 wherein the cancer is lung cancer metastatic lesions of the liver.

11. The method according to claim 8 wherein the cancer is lung cancer metastatic lesions of the lymph nodes.

12. The method according to claim 7 wherein the SGLT2 inhibitor has the structure

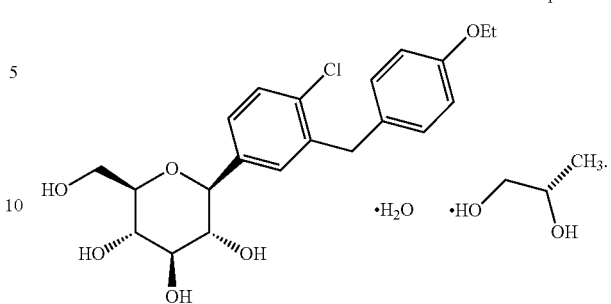

Compound Ia

13. A method for treating cancers that express SGLT2 levels higher than normal cells in a mammal comprising administering to the mammal in need of such treatment a therapeutically effective amount of an SGLT2 inhibitor having the structure or a prodrug ester thereof, or a pharmaceutically acceptable salt thereof and a cytotoxic agent where the cytotoxic agent is administered prior to, after, or concurrently with the SGLT2 inhibitor.

14. The method according to claim 13 wherein the mammal is a human.

15. The method according to claim 14 wherein the cancer is lung cancer metastatic lesions.

16. The method according to claim 14 wherein the cancer is lung cancer metastatic lesions of the liver.

17. The method according to claim 14 wherein the cancer is lung cancer metastatic lesions of the lymph nodes.

18. The method according to claim 13 wherein the SGLT2 inhibitor has the structure

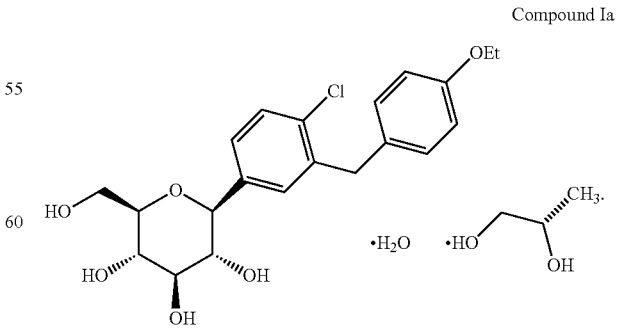

Compound Ia

19. A method for treating cancers that express SGLT2 levels higher than normal cells in a mammal comprising administering to the mammal in need of such treatment a therapeutically effective amount of a pharmaceutical composition comprising an SGLT2 inhibitor having the structure

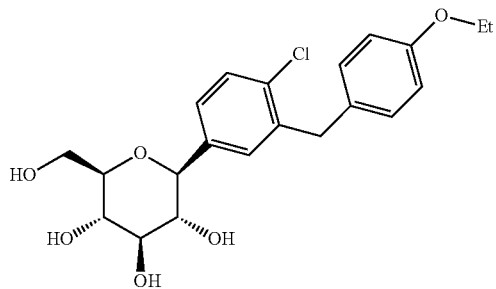 [SMILES: CCOc1ccc(Cc2cc([C@@H]3O[C@H](CO)[C@@H](O)[C@H](O)[C@H]3O)ccc2Cl)cc1]

or a prodrug ester thereof, or a pharmaceutically acceptable salt thereof, a cytotoxic agent and at least one pharmaceutically acceptable carrier, excipient, or diluent.

20. The method according to claim 19 wherein the mammal is a human.

21. The method according to claim 20 wherein the cancer is lung cancer metastatic lesions.

22. The method according to claim 20 wherein the cancer is lung cancer metastatic lesions of the liver.

23. The method according to claim 20 wherein the cancer is lung cancer metastatic lesions of the lymph nodes.

24. The method according to claim 19 wherein the SGLT2 inhibitor has the structure

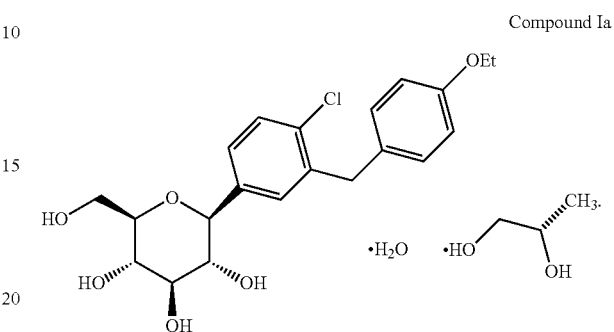

Compound Ia

* * * * *